US006096049A

United States Patent [19]

McNeirney et al.

[11] Patent Number: 6,096,049

[45] Date of Patent: Aug. 1, 2000

[54] LIGHT GUIDING DEVICE AND METHOD

[75] Inventors: John C. McNeirney, Fairburn, Ga.; Michael K. Landi, Kenmore, N.Y.

[73] Assignee: Minrad Inc., Buffalo, N.Y.

[21] Appl. No.: 09/122,922

[22] Filed: Jul. 27, 1998

[51] Int. Cl.[7] .......... A61B 19/00

[52] U.S. Cl. .......... 606/130; 600/424; 33/286; 33/DIG. 21; 356/153

[58] Field of Search .......... 606/130; 600/424, 600/478, 114; 604/116, 606, 20, 10, 129, 130; 33/286 C, DIG. 21; 356/153, 399

[56] References Cited

U.S. PATENT DOCUMENTS

| | | | |
|---|---|---|---|
| 4,651,732 | 3/1987 | Frederick | 604/20 |
| 5,031,203 | 7/1991 | Trecha | 378/205 |
| 5,116,344 | 5/1992 | Sundqvist | 606/130 |
| 5,320,111 | 6/1994 | Livingston | 606/130 |
| 5,553,115 | 9/1996 | Odaka et al. | 378/206 |
| 5,598,269 | 1/1997 | Kitaevich et al. | 606/130 |
| 5,810,841 | 9/1998 | McNeirney et al. | 606/130 |

*Primary Examiner*—Gene Mancene
*Assistant Examiner*—Pedro Philogene
*Attorney, Agent, or Firm*—Hodgson, Russ, Andrews, Woods & Goodyear LLP

[57] ABSTRACT

The present invention provides an instrument adapted for alignment with a light beam, which instrument includes an instrument body having a point of entry of the light beam, a light conducting channel, and a sensing element carried by the instrument and being spaced from the point of entry of the light beam. The sensing element serves to provide indication of alignment or misalignment between the instrument and the light beam. The light beam travels inside the instrument along the light conducting channel extending from the point of entry to the sensing element. One or more light guiding devices are disposed inside the light conducting channel to increase precision of alignment between the instrument and the light beam. The light guiding device has a wall forming a guiding passage inside the guiding device. When disposed inside the instrument, the wall of the guiding device blocks non-aligned light beams from reaching the sensing element, while allowing the aligned light beams to propagate along a predetermined path through the guiding passage inside the instrument and reach the sensing element.

29 Claims, 5 Drawing Sheets

LIGHT GUIDING DEVICE AND METHOD

BACKGROUND OF THE INVENTION

1. Field of the Invention

The present invention relates in general to the art of guiding a light beam in a light conducting medium and, in particular, to a structure inside a light conducting medium directing the light beam along a predetermined path.

2. Background Art

Visible light beams, such as lasers, are often used in various procedures involving imaging equipment to locate a point of entry and an angle of approach to a subsurface target, such as a tumor or any other area inside the body of a patient. In these procedures a visible light beam usually serves as a visible guide for accessing the subsurface target with an invasive instrument which is maintained in an aligned position with the light beam. In computer tomography or fluoroscopically guided procedures imaging is used to localize and determine the position of a subsurface target requiring treatment or medical investigation. Once the position of a subsurface target is determined, a doctor then uses the imaging equipment to select the desired path of access to the subsurface target with invasive instruments such as needles, drainage catheters, localization wires or other biopsy tools to perform necessary procedures. After the desired path is selected, the doctor guides the invasive instrument along the path to the target by maintaining the invasive instrument in alignment with that selected path.

As a practical matter, constantly maintaining the invasive instrument in alignment with the selected path during a medical procedure may be difficult. A solution to the alignment maintenance problem is disclosed in patent application Ser. No. 08/859,380 "Energy Guided Apparatus And Method With Indication of Alignment", which application is incorporated herein by reference. Described in that application is a visible light beam, such as a laser beam, directed along a predetermined path at a preselected target within a patient's body, therefore illuminating the path and making it visible to a doctor. The invasive instrument described in that application has a light conducting channel that allows the light beam to enter the instrument through an opening and propagate inside the light conducting channel. If the light beam and the invasive instrument are properly aligned, the light beam travels through the channel and reaches a sensor which indicates the alignment by dispersing visible light or by any other means suitable for a particular application.

The accuracy of alignment of the visible light beam and the invasive instrument is important for performing a medical procedure correctly, precisely and efficiently. Given a very high energy concentration of laser beams that are commonly employed in medicine, a non-aligned laser beam reflected from the interior surfaces of the light conducting channel of the invasive instrument can still reach the sensor and falsely indicate alignment between the invasive instrument and the focused laser beam. This, in turn, greatly degrades the accuracy of alignment of the laser beam and the instrument and results in incorrect performance of a medical procedure. For example, a 5 mW laser focused to a 1 mm spot at a distance of 750 mm from the laser source has a visible light intensity equivalent to the light intensity of a 35,000 W bulb viewed at 750 mm. As a result, such an intense non-aligned laser beam can be reflected from the interior surfaces of the conducting channel and falsely indicate alignment of the invasive instrument and the focused laser beam.

Therefore, a need exists to have an invasive instrument with such an improved light conducting channel that will reduce the probability that a nonaligned visible light beam gets reflected from the interior surface of the channel and causes a false indication of alignment after reaching and illuminating the sensor.

SUMMARY OF THE INVENTION

It is therefore an object of the present invention to increase the accuracy of alignment of a visible light beam and an invasive instrument by defining a path inside the instrument along which only a substantially aligned light beam will propagate and reach an alignment indicator in the form of a sensor responsive to illumination.

It is also an object of the present invention to exclude possible false positive indications of alignment by introducing a structure inside the instrument, which structure will prevent misaligned visible light beams from contacting the alignment indicator.

It is yet another object of the present invention to decrease the probability of non-aligned visible light beams contacting the alignment indicator by introducing a method of guiding a light beam inside the invasive instrument.

Yet another object of the present invention is to incorporate the structure for guiding the light beam into different types of invasive instruments.

The present invention provides an instrument adapted for alignment with a light beam, which instrument includes an instrument body having a point of entry of the light beam, a light conducting channel and a sensing means carried by the instrument and being spaced from the point of entry of the light beam. The sensing means serves to provide indication of alignment or misalignment between the instrument and the light beam. The light beam travels inside the instrument along the light conducting channel extending from the point of entry to the sensing means. One or more light guiding devices are disposed inside the light conducting channel to increase precision of alignment between the instrument and the light beam. The light guiding device has a wall forming a guiding passage inside the guiding device. When disposed inside the instrument, the wall of the guiding device blocks non-aligned light beams from reaching the sensing means, while allowing the aligned light beams to propagate along a predetermined path through the passage inside the instrument and reach the sensing means.

There is also provided a method of aligning a visible light beam and an invasive instrument in a targeting system. The targeting system generates the light beam which enters the invasive instrument at a point of entry and propagates along within the instrument inside a light conducting channel. The method calls for providing at least one light guiding element which defines a predetermined path of propagation of the light beam within the instrument. When the instrument is positioned in a manner such that the light beam travels within the instrument along the path defined by one or more guiding devices, a user will observe the response of a sensing means carried by the instrument. The response indicates either alignment or misalignment between the light beam and the instrument.

These and other objects and advantages of the present invention will become increasingly more apparent to those skilled in the art by reference to the following description and to the accompanied drawings.

BRIEF DESCRIPTION OF THE DRAWING FIGURES

DETAILED DESCRIPTION OF THE PREFERRED EMBODIMENT

Figures 1, 1A:
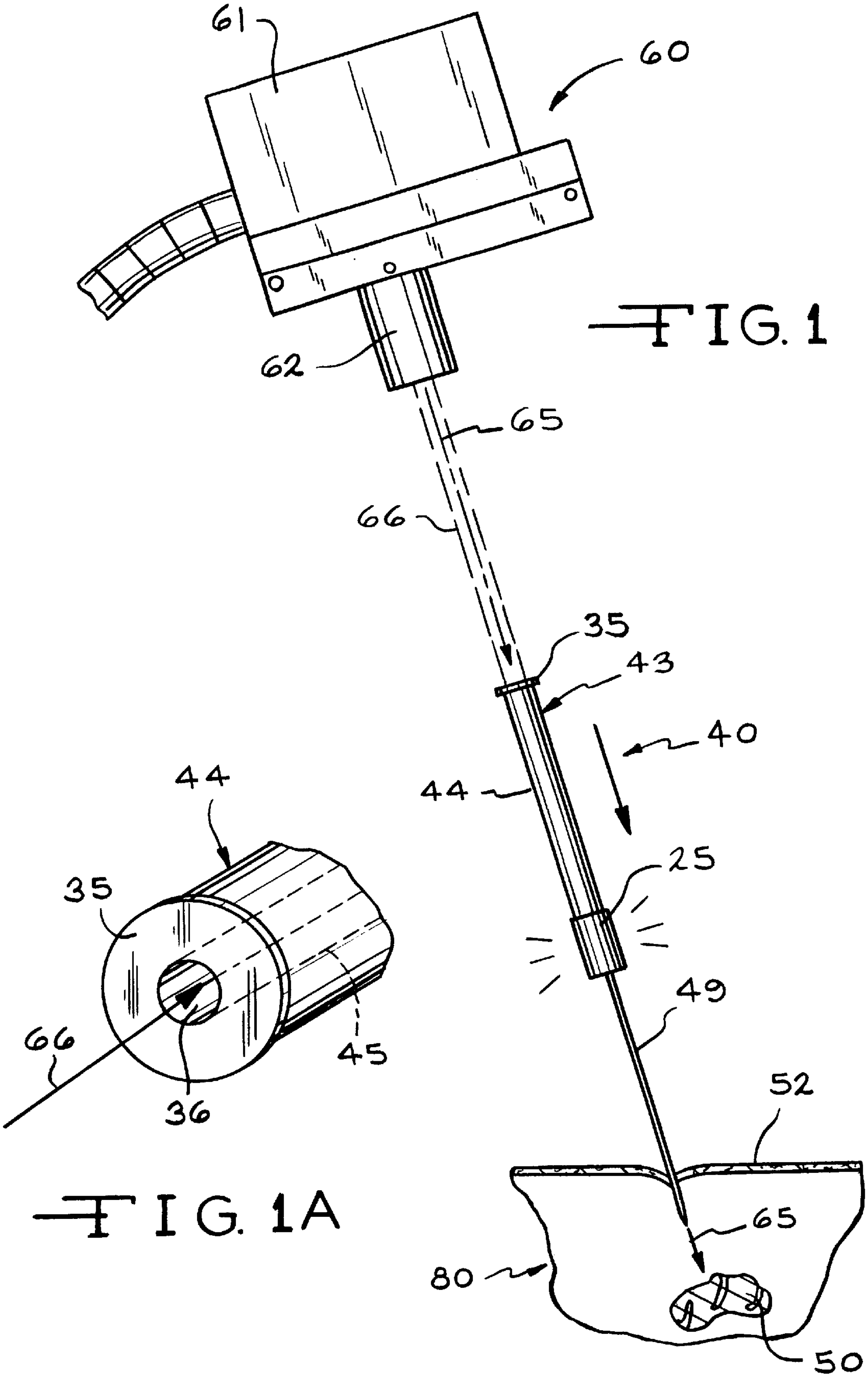
FIG. 1 is a schematic representation of a targeting system and an invasive instrument for use with a light guiding device of the present invention.
FIG. 1A is a perspective view of the end of an invasive instrument where a light beam enters the instrument.

Shown in FIG. 1 is an example of an invasive instrument 40 for use with a visible light beam 66 to access a subsurface target 50. Such an invasive instrument can be a syringe, a biopsy needle, a cannula, a drill or a similar instrument. As shown in FIG. 1, a targeting system 60, of a type preferred for use in conjunction with the instrument of the present invention, provides visible light beam 66 which is directed along a predetermined path 65 toward subsurface target 50. Most often the location of subsurface target 50 is determined through the use of imaging equipment such as an x-ray system, a computer tomograph or a magnetic resonance imaging machine.

Visible light beam 66 is incident on surface 52 of an object 80 to be penetrated at a predetermined point and a predetermined angle. The point and angle together help define the line of sight path 65, also referred to as predetermined path 65, to subsurface target 50. Visible light beam 66, when directed along path 65 to target 50 , can be utilized to guide invasive instrument 40 along path 65 to access target 50 in a manner which will be described.

Targeting system 60 is preferably of the dual radiation targeting system type described in U.S. Pat. No. 5,212,720 to Landi et al, which is incorporated herein by reference. In such a targeting system, subsurface regions of an x-ray transparent, but optically opaque object, as shown at 80, are targeted along predetermined path 65, obtained by the use of two radiation sources, an x-ray source 61 and a visible light source 62, preferably a laser source.

Once targeting system 60 has directed visible light beam 66 along predetermined path 65 to subsurface target 50, an invasive instrument such as that shown at 40 may be used to penetrate surface 52 to access subsurface target 50. Surface 52 can be a patient's body, or a structure such as a wall, hull or any other surface structure through which it is desired to introduce an invasive instrument in order to access a subsurface target.

As illustrated in FIGS. 1 and 1A, in accordance with the preferred embodiment of the present invention invasive instrument 40 comprises a body 43 with an opening 36 at an end 35 of body 43. A radiation conducting medium 44 associated with body 43 comprises a conducting channel 45 along which visible light beam 66 can propagate. Visible light beam 66 enters instrument 40 through opening 36 and travels inside the instrument along channel 45 until it reaches a sensing means 25. Sensing means 25 may be made of any material responsive to visible light, or may be a sensor responsive to electromagnetic transmissions of other types. Sensing means 25 may provide a visual indication in response to the radiation it receives, or it may provide an audible or any other indication in response to the received radiation. All of these variations are intended to remain within the scope of the present invention.

Visible light beam 66 may be any kind of radiation that is capable of illuminating predetermined path 65 and making it visible, such as, for example, a collimated light beam, or a laser beam. The preferred embodiment of the present invention calls for use of a laser beam.

As will be appreciated by those skilled in the art, a wide variety of instruments and tools having various means for percutaneously accessing a subsurface target similar to that shown in FIG. 1 at 49, may comprise body 43 with opening 36, conducting channel 45, and sensing means 25. In addition to medical instruments, these instruments include drills, bores, punches and any other implement used to penetrate a surface to reach a subsurface target.

The detailed description of the structure of an invasive instrument of the type of instrument 40, as well as the detailed description of the method of operation of such an instrument, is provided in patent application Ser. No. 08/859,380 "Energy Guided Apparatus And Method With Indication of Alignment", which application is incorporated herein by reference.

Figure 2:
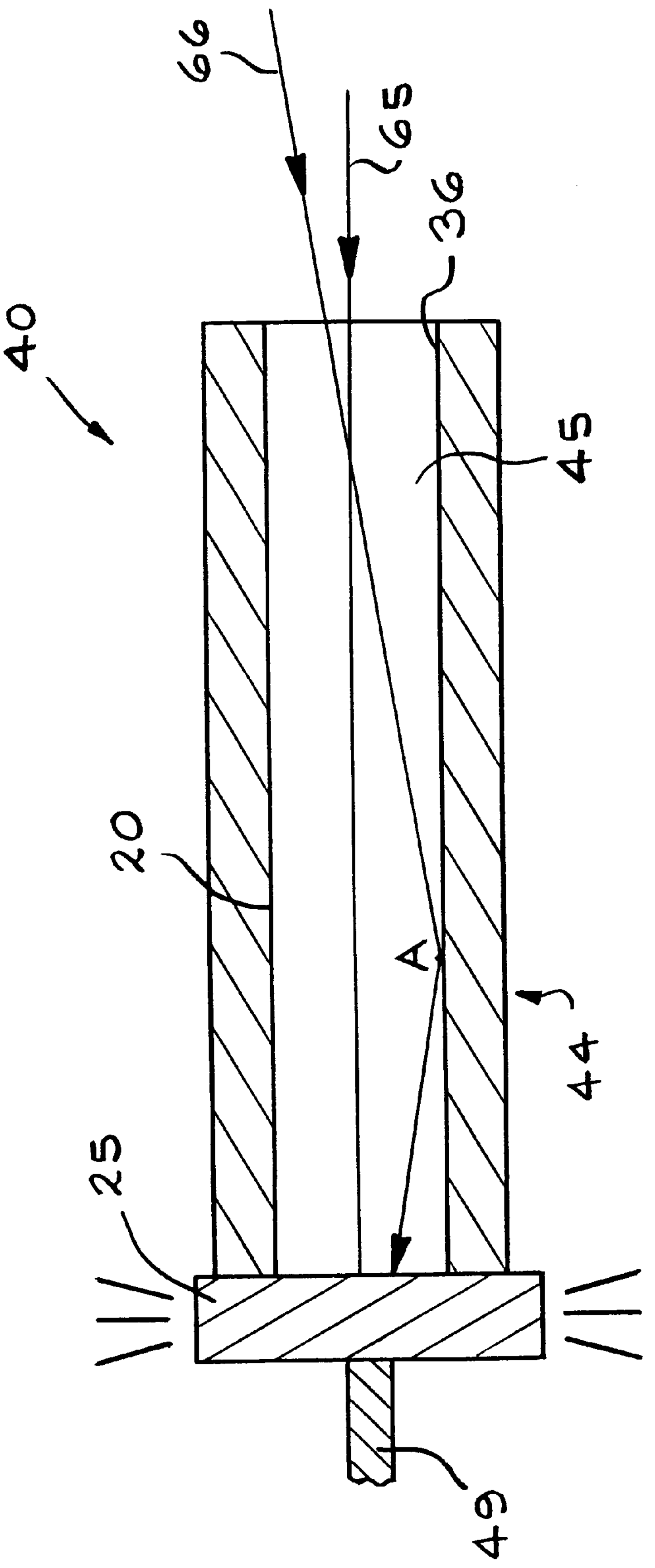
FIG. 2 is a schematic cross-sectional view of a light guiding channel illustrating a false-positive indication of alignment.

Radiation conducting medium 44 of invasive instrument 40 comprises internal surface 20 defining conducting channel 45, as illustrated in FIG. 2. As can be seen in FIG. 2, visible light beam 66 entering conducting channel 45 is not aligned with predetermined path 65. Nevertheless, it is possible for a highly intensive light beam 66 to reflect from internal surface 20 at point A and reach sensing means 25, activating the sensing means and causing it to falsely indicate alignment between light beam 66 and invasive instrument 40.

Figure 3:
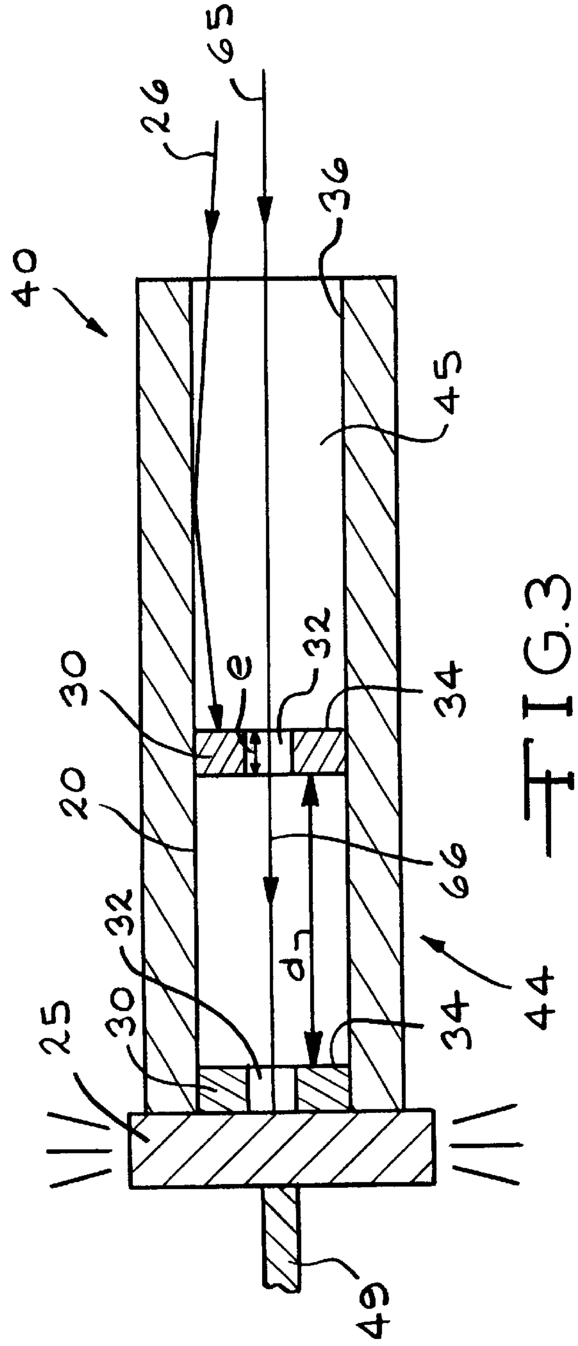
FIG. 3 is a schematic cross-sectional view of an invasive instrument with two light guiding devices of the present invention in a light guiding channel.
Figure 5:
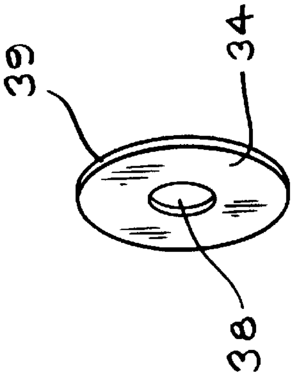
FIG. 5 is a perspective view of another form of light guiding device of the present invention.
Figure 4:
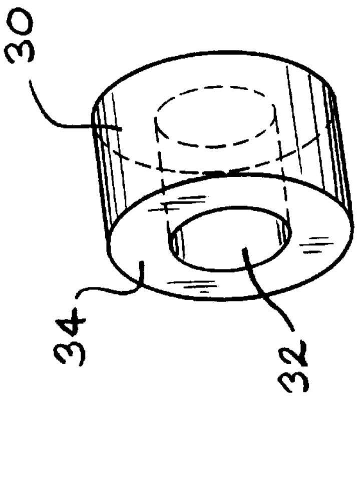
FIG. 4 is a perspective view of one form of a light guiding device of the present invention.

To prevent unaligned light beams from reaching sensing means 25 in a situation illustrated in FIG. 2, a light guiding device is provided in light conducting channel 45. For example, FIG. 3 illustrates invasive instrument 40 with a plurality of light guiding devices 30 which increase the precision of alignment between invasive instrument 40 and visible light beam 66. Depending on a particular design of an invasive instrument or a particular setting in which it is used, the instrument may include one or more guiding devices 30. Each light guiding device comprises a body of optically opaque or substantially opaque material extending across the cross-sectional area of channel 45 and having an opening or passage therethrough of a size and location which allows travel therethrough of only those radiation or light beams coincident or substantially coincident with path 65. As shown in FIGS. 3, 4, and 5, guiding device 30 comprises a wall 34 surrounding a path defining channel 32. Guiding device 30 of the present invention is of such size and shape that it is fixed inside conducting channel 45 and remains there during the life of the instrument. This can be accomplished by a friction fit between the periphery of device 30 and the internal surface 20 of channel 45 or by cementing or otherwise bonding the periphery of device 30 to surface 20.

The purpose of guiding device 30 is to allow only such light beam 66 which propagates substantially along predetermined path 65 to travel inside conducting channel 45 through path defining channel 32 and reach sensing means 25. Light beams which are not directed substantially along predetermined path 65, as shown in FIG. 3 at 26, will impinge upon optically opaque wall 34 and, therefore, will not propagate inside invasive instrument 40 beyond guiding device 30 and will not illuminate sensing means 25.

When conducting channel 45 contains several spaced apart light guiding devices, as in FIG. 3, a distance d between the adjacent guiding devices and a length 1 of path defining channel 32 preferrably are not multiples of each other in order for a non-aligned visible light beam to be trapped by the guiding devices.

Thus, each light guiding device may be viewed as a collimating trap which allows only properly aligned beams to travel therethrough and which traps or blocks the beams which are not properly aligned.

Generally, guiding device 30 can be of various shapes and sizes, depending on the requirements of a particular application or manufacturing constraints. In the preferred embodiment of the present invention a substantially cylindrical guiding device 30, of the type shown in FIG. 4, conforms to the substantially cylindrical shape and size of conducting channel 45 of invasive instrument 40. When guiding device 30 is disposed inside conducting channel 45, path defining channel 32 of the guiding device is substantially coaxial with conducting channel 45, as illustrated in FIG. 3. Light beam 66 traveling inside conducting channel 45 with one or more guiding devices 30 will reach sensing means 25 only if that light beam 66 propagates substantially along predetermined path 65. Reflected light beams, such as beam 26, which are not in alignment with predetermined path 65, will reach wall 34 of guiding device 30 and will not propagate further inside conducting channel 45.

Guiding device 30 may also be in the form of a thin partition 39 with an opening, as illustrated in FIG. 5. An opening 38 in partition 39 serves the same purpose of allowing only the light beams substantially coaxial with predetermined path 65 to propagate inside conducting channel 45 and reach sensing means 25. The choice of a particular embodiment of guiding device 30 may be dictated by different desired design features of the invasive instrument or by particular conditions in which the instrument is used.

Figure 6:
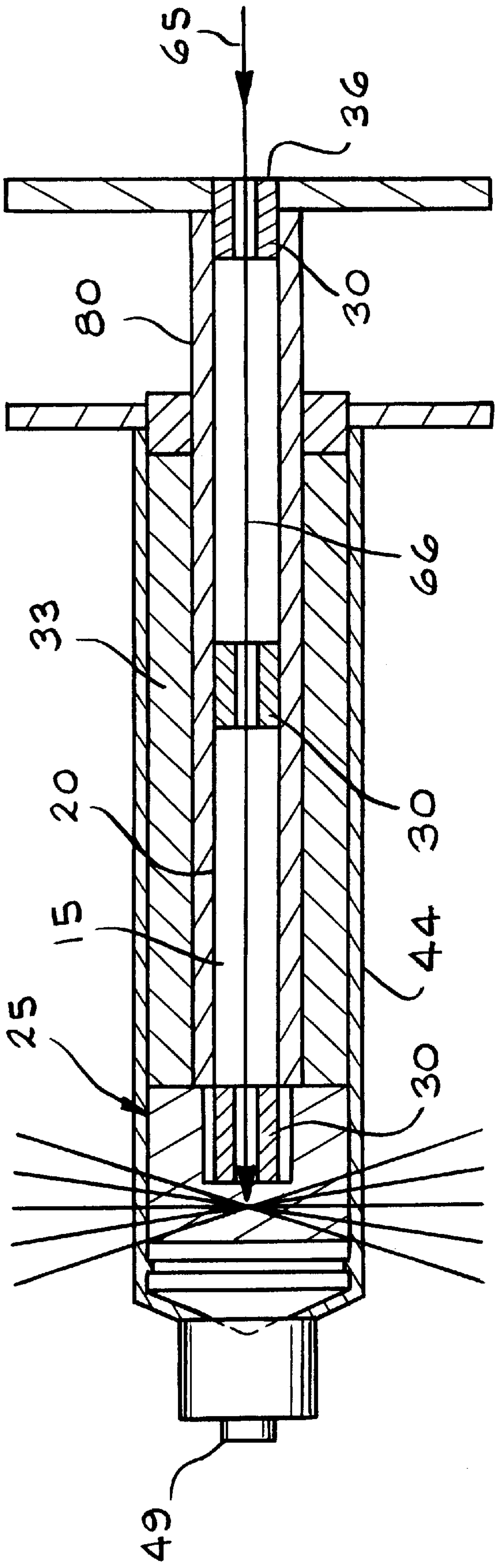
FIG. 6 is a schematic cross-sectional view of a syringe embodiment with light guiding devices.

Another embodiment of an invasive instrument according to the present invention is a syringe, as shown in FIG. 6, with a plunger 80 which moves inside a cylinder 33 to which penetrating element 49, such as a needle, is attached. Plunger 80 comprises light conducting channel 45, a plurality of guiding devices 30 for increasing alignment precision between the syringe and visible light beam 66, and sensing element 25 for indicating alignment. In this embodiment light guiding devices 30 are situated inside light conducting channel 45 in plunger 80. The shape, size and number of the guiding devices can vary depending on the design features of a particular syringe. The type of the guiding device used in a syringe embodiment of the present invention is similar to the one depicted in FIGS. 4–5 described above. The number of guiding devices 30 in the light conducting channel of the syringe can also vary, depending on the desired precision of alignment and manufacturing constraints.

The light guiding device of the present invention can be manufactured from any optically opaque material, such as plastic or metal, suitable for a desired application.

As those skilled in the art will appreciate based on the foregoing description, the light guiding device of the present invention can be used in a variety of invasive instruments having needles such as fluid aspiration needles (such as amniocentesis needles) and other needles which may be used in this invention. Also the present invention may be used to increase the alignment precision of instruments employed in various biopsy techniques, including cytologic aspiration, fluid aspiration, histological biopsies, as well as coaxial percutaneous biopsy techniques.

Furthermore, the present invention may be used with any invasive instrument wherever improved guidance mechanisms are desired. For example, trocars, insertable scopes, catheters and the like may be provided with a radiation conducting channel, one or more light guiding devices and a sensing element, responsive to a radiation beam, such as a visible light beam directed along a predetermined path to a subsurface target.

Figure 7:
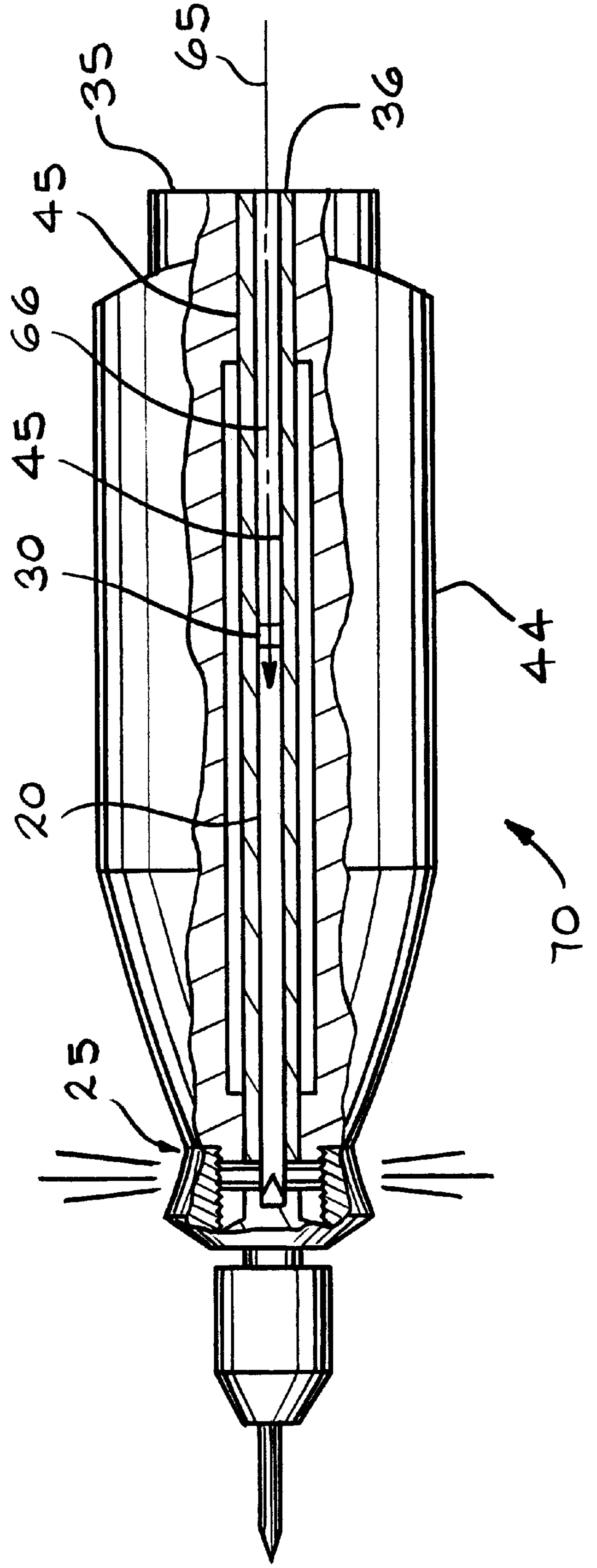
FIG. 7 is a cross-sectional view of a light guiding channel with a sensor according to another embodiment of the present invention.

FIG. 7 illustrates yet another invasive instrument with a light guiding device in accordance with the present invention, a drill instrument 70, having light conducting channel 45, light guiding device 30, and sensing element 25. Energy conducting medium 44 is provided to include light conducting channel 45 having opening 36 at end 35.

Light conducting channel 45 extends from opening 36 to sensing element 25, comprising light conducting channel 45 in coaxial alignment with the axis of a drill bit 24. Light guiding device 30 disposed inside channel 45, similarly to the disposition of the light guiding devices described in reference to FIGS. 3–5.

Providing light guiding devices 30 of the present invention, each in the form of an optically opaque body having a passage therethrough, and located within light conducting channel 45, enables opening 36 to be maintained at a size allowing the user to easily manipulate the instrument while aligning it with light beam 66, the size of opening 36 being larger than the size of the opening or passage through light guiding device 30. In addition, providing light guiding device 30 within light conducting channel 45 is believed to be advantageous as compared to only providing light absorbing or dispersing formations or coatings on surface 20 without one or more light guiding devices 30. That is because the intensity of laser beams in many instances can be sufficient to overcome the effect of such surface formations and/or coatings and allow improperly aligned beams to reach sensing means 25. To improve blocking of non-aligned beams, the present invention provides for use of light guiding devices together with sufficiently non-reflective surface 20, which use improves the chances that a non-aligned light beam will be trapped inside channel 45 before reaching sensing means 25. Surface 20 can be made non-reflective by using light absorbing or light dispersing materials well known to those skilled in the art.

It is therefore apparent that the present invention accomplishes its intended objects. While embodiments of the present invention have been described in detail, that is for the purpose of illustration, not limitation.

What is claimed is:

1. In an invasive instrument having a body with an opening at one end, and having a region therein for conducting a radiation beam entering the invasive instrument through the opening, and a sensing element carried by the instrument and spaced from the opening for indicating either alignment or misalignment between the instrument and the radiation beam, the radiation conducting region comprising:

a channel disposed inside the body of the invasive instrument in such a way that it allows the radiation beam to propagate inside the instrument and reach the sensing element; and at least one guiding element disposed inside the channel between the opening and the sensing element, the guiding element defining a predetermined path of propagation of the radiation beam inside the channel so that the invasive instrument and the radiation beam are in alignment.

2. The radiation conducting region of claim 1, wherein the channel is substantially cylindrical.

3. The radiation conducting region of claim 2, wherein the guiding element is substantially cylindrical and coaxial with the channel.

4. The radiation conducting region of claim 1 further comprising a plurality of guiding elements at spaced locations along the channel.

5. The radiation conducting region of claim 4, wherein the guiding elements are of substantially similar shape and size, the guiding elements being evenly spaced in such a way that a distance between two adjacent guiding elements and a dimension of a guiding element collinear with the predetermined path are not multiples of each other.

6. The radiation conducting region of claim 4, wherein the guiding elements are unevenly spaced.

7. The radiation conducting region of claim 1, wherein the guiding element is made of optically opaque material.

8. The radiation conducting region of claim 1, wherein the shape of the guiding element conforms to the shape of the channel.

9. The radiation conducting region of claim 1, wherein the energy beam is a visible light beam.

10. The radiation conducting region of claim 1, wherein the energy beam is a laser beam.

11. An apparatus for guiding a radiation beam inside a radiation conducting body associated with an instrument and having an opening through which the radiation beam enters the radiation conducting body, the apparatus comprising:

an elongated channel disposed inside the radiation conducting body in such a way that the radiation beam can enter the channel through the opening and propagate inside the channel, the channel having a longitudinal axis; and at least one radiation guiding element disposed inside the channel, the guiding element defining a predetermined path of propagation of the radiation beam inside the channel and substantially in alignment with the longitudinal axis of the channel.

12. The apparatus of claim 11 further comprising a plurality of guiding elements at spaced locations along the channel.

13. The apparatus of claim 11 further comprising a sensing element responsive being contacted by the radiation beam, the sensing element being carried by the energy conducting medium and spaced from the opening.

14. The apparatus of claim 11, wherein the guiding element is of optically opaque material and has an opening defining the predetermined path of propagation.

15. The apparatus of claim 11, wherein the channel is substantially cylindrical.

16. The apparatus of claim 11, wherein the shape of the guiding element conforms to the shape of the channel.

17. The apparatus of claim 11, wherein the energy beam is a visible light beam.

18. The apparatus of claim 11, wherein the energy beam is a laser beam.

19. A method of guiding a radiation beam in a radiation conducting body associated with an instrument and having an elongated channel disposed therein and having a longitudinal axis, the method comprising:

providing at least one radiation guiding element of such a shape that the guiding element can be received inside the channel of the radiation conducting body; and positioning the radiation guiding element inside the channel so that the guiding element defines a predetermined path along which the radiation beam propagates in the radiation conducting body.

20. The method of claim 19 further comprising a step of providing a plurality of guiding elements at spaced locations along and inside the channel.

21. The method of claim 19, wherein the radiation beam is a collimated visible light beam.

22. An instrument adapted for alignment with a light beam, the instrument comprising:

an instrument body having a point of entry for the light beam;

a sensing means carried by the instrument body, the sensing means being spaced from the point of entry of the light beam and providing an indication of either alignment or misalignment between the instrument and the light beam;

a conducting means associated with the instrument body for directing the light beam from the point of entry to the sensing means; and at least one guiding element disposed inside the conducting means, the guiding element defining a predetermined path of propagation of the light beam along within the conducting means.

23. The instrument according to claim 22, wherein the conducting means comprises an elongated light conducting channel within the instrument body.

24. A method of aligning a light beam and an instrument in a system comprising means for providing a light beam, the instrument having a sensing means carried by the instrument and an entry point for the light beam, the method comprising the steps of:

providing the light beam;

providing at least one guiding element which defines a path of propagation of the light beam within the instrument;

positioning the instrument in a manner such that the light beam travels into the instrument through the point of entry; and observing the response of the sensing means, the response being indicative of either alignment or misalignment between the light beam and the instrument.

25. In a system comprising means for directing an radiation beam at a preselected target within a body and wherein an invasive instrument is employed to access the preselected target by penetrating the surface of the body, and wherein the radiation beam is incident upon the surface of the body at a desired penetration point, and wherein the direction of the radiation beam indicates the desired angle and axis for the invasive instrument to penetrate the body, the invasive instrument comprising:

an elongate radiation conducting portion having a distal end and a proximal end, said elongate radiation conducting portion adapted to receive the radiation beam at said proximal end and to conduct the radiation beam to said distal end;

means for percutaneously accessing the target;

radiation responsive means interposed between said means for percutaneously accessing the target and said distal end of said radiation conducting portion, said radiation responsive means serving to disperse visible light whenever said means for percutaneously accessing the target is in axial alignment with the radiation beam; and at least one guiding element disposed in the radiation conducting portion between the radiation responsive means and the distal end for defining a predetermined path of propagation of the radiation beam along within the radiation conducting portion.

26. An instrument for insertion of a needle into a body for use with an imaging system having means for directing a light beam at a preselected target within the body and an instrument having an entry point of the light beam, the instrument comprising:

an elongate light conducting portion having a distal end and a proximal end, said elongate light conducting portion adapted to receive the incident beam of light at said proximal end and to conduct the incident beam of light to said distal end;

a needle portion collinear and coaxial with said elongate light conducting portion;

light responsive means interposed between said needle portion and said distal end of said elongate light conducting portion for dispersing the light beam whenever said elongate light conducting portion is in axial alignment with the light beam; and at least one guiding element disposed in the light conducting portion between the light responsive means and the distal end for defining a predetermined path of propagation of the light beam along within the light conducting portion.

27. A device for penetrating a subsurface target along a predetermined path and at a predetermined penetration angle, the device comprising:

means for penetrating a surface located at one end of said device;

an elongate radiation conducting portion located at the other end of said device and coupled to said penetrating means;

means for dispersing visible light interposed between said elongate radiation conducting portion and said means for penetrating a surface;

said elongate radiation conducting portion adapted to include a linearly extending radiation conducting channel extending from the proximal end of said elongate radiation conducting portion and terminating within said means for dispersing visible light, said linearly extending radiation conducting channel being coaxial and collinear with said means for penetrating a surface; and at least one guiding element disposed in the channel for defining a predetermined path of propagation of a radiation beam along within the channel.

28. A method of providing accurate guidance along a predetermined path of an invasive instrument in invasive procedures in which the instrument is inserted axially into a body, the method comprising the steps of:

illuminating the predetermined path with a light beam;

aligning the instrument axially with the light beam such that visible light is emitted from the instrument;

causing the light beam to enter the invasive instrument such that visible light is emitted from a sensing means carried by the instrument when the instrument is in axial alignment with the illuminated predetermined path;

guiding the light beam after it enters the invasive instrument along a predetermined path of propagation within the instrument;

moving the aligned instrument along the predetermined path while maintaining the axial alignment of the instrument with the light beam by monitoring the visible light emitted from the instrument; and inserting the aligned instrument into the body while maintaining the axial alignment of the instrument with the light beam by monitoring the visible light emitted from the instrument.

29. In a system comprising means for directing a radiation beam at a preselected target within a body and wherein an invasive instrument is employed to access the preselected target by penetrating the surface of the body, and wherein the radiation beam is incident upon the surface of the body at a desired penetration point, and wherein the direction of the radiation beam indicates the desired angle and axis for the invasive instrument to penetrate the body, the invasive instrument comprising:

an elongate radiation conducting portion having a distal end and a proximal end, said elongate radiation conducting portion adapted to receive the radiation beam at said proximal end and to conduct the radiation beam to said distal end;

means for percutaneously accessing the target;

radiation responsive means interposed between said means for percutaneously accessing the target and said distal end of said radiation conducting portion, said radiation responsive means indicating proper alignment between said means for percutaneously accessing the target and the radiation beam; and at least one guiding element disposed in the radiation conducting portion between the radiation responsive means and the distal end for defining a predetermined path of propagation of the radiation beam along within the radiation conducting portion.

* * * * *